(12) United States Patent
Rudie et al.

(10) Patent No.: US 10,755,596 B1
(45) Date of Patent: Aug. 25, 2020

(54) MEDICAL CARE EDUCATION EMOTIONAL SUPPORT, AND DEVELOPMENT ASSISTANCE DEVICE

(71) Applicants: Christina Osborn Rudie, Bakersfield, CA (US); Paul W. Scott, IV, San Luis Obispo, CA (US)

(72) Inventors: Christina Osborn Rudie, Bakersfield, CA (US); Paul W. Scott, IV, San Luis Obispo, CA (US)

( * ) Notice: Subject to any disclaimer, the term of this patent is extended or adjusted under 35 U.S.C. 154(b) by 496 days.

(21) Appl. No.: 15/530,677

(22) Filed: Feb. 3, 2015

(51) Int. Cl.
| | |
|---|---|
| *G09B 19/00* | (2006.01) |
| *G06F 19/00* | (2018.01) |
| *G09B 5/06* | (2006.01) |
| *G06Q 50/20* | (2012.01) |
| *G06F 3/0483* | (2013.01) |
| *B42D 3/12* | (2006.01) |
| *A63H 33/38* | (2006.01) |

(52) U.S. Cl.
CPC ......... *G09B 19/00* (2013.01); *G06F 19/3418* (2013.01); *G09B 5/062* (2013.01); *A63H 33/38* (2013.01); *B42D 3/123* (2013.01); *G06F 3/0483* (2013.01); *G06Q 50/20* (2013.01); *G09B 5/06* (2013.01)

(58) Field of Classification Search
CPC .......... G09B 5/062; G09B 5/06; G09B 19/00; B42D 3/123; A63H 33/38; G06F 3/0483; G06F 19/3418; G06Q 50/20
USPC ....................................................... 434/236
See application file for complete search history.

(56) References Cited

U.S. PATENT DOCUMENTS

| | | | | |
|---|---|---|---|---|
| 5,707,240 A | * | 1/1998 | Haas ...................... | B42D 3/123 434/308 |
| 5,774,861 A | * | 6/1998 | Spector .................. | A47D 15/00 369/19 |
| 5,787,617 A | * | 8/1998 | Testa ........................ | G09F 1/10 281/38 |
| 6,421,524 B1 | * | 7/2002 | Padgett .................. | B42D 3/123 434/317 |
| 8,297,800 B1 | * | 10/2012 | Little ..................... | A47G 33/00 362/253 |
| 8,967,376 B1 | * | 3/2015 | Lewbel ................. | G06F 1/1628 206/320 |
| 2001/0046659 A1 | * | 11/2001 | Oster ................... | G09B 17/006 434/178 |
| 2002/0133350 A1 | * | 9/2002 | Cogliano ............... | G09B 19/04 704/270 |
| 2003/0022143 A1 | * | 1/2003 | Kirwan .................. | G09B 5/062 434/317 |
| 2003/0184996 A1 | * | 10/2003 | Marshall ................ | A45D 42/16 362/144 |
| 2004/0016809 A1 | * | 1/2004 | Song ...................... | G06F 3/0224 235/449 |
| 2006/0046935 A1 | * | 3/2006 | Burrows ................ | B41M 5/035 503/227 |

(Continued)

Primary Examiner — Jack Yip (57) ABSTRACT

A multi-page illustrated and written book printed on synthetic paper with an electronics module that can record sounds through one or more microphones to solid-state, digital memory and playback pre-recorded or user recorded audio data from the digital memory device through one or more speakers is disclosed. The book may include one or more of the following either on the front or back cover or on any of the plurality of pages inside the book: mirror, signature page, pocket page, or high-contract geometric patterns.

20 Claims, 5 Drawing Sheets

(56) References Cited

U.S. PATENT DOCUMENTS

| | | | | |
|---|---|---|---|---|
| 2007/0085324 A1* | 4/2007 | Locker | ............ | B42D 3/12 |
| | | | | 281/15.1 |
| 2008/0015847 A1* | 1/2008 | Lallouz | ............ | G06F 15/16 |
| | | | | 704/201 |
| 2008/0217904 A1* | 9/2008 | Wright | ............ | A63H 33/38 |
| | | | | 281/43 |
| 2010/0028843 A1* | 2/2010 | Currington | ............ | G09B 5/062 |
| | | | | 434/317 |
| 2011/0059426 A1* | 3/2011 | Mamigonians | ............ | G09B 5/062 |
| | | | | 434/317 |
| 2012/0256408 A1* | 10/2012 | Malia | ............ | A63H 33/38 |
| | | | | 283/63.1 |
| 2013/0050164 A1* | 2/2013 | Rericha | ............ | G06F 1/1626 |
| | | | | 345/205 |
| 2013/0072080 A1* | 3/2013 | Garbos | ............ | A63H 33/26 |
| | | | | 446/26 |
| 2016/0068002 A1* | 3/2016 | Keller | ............ | G06F 3/147 |
| | | | | 386/201 |

\* cited by examiner

MEDICAL CARE EDUCATION EMOTIONAL SUPPORT, AND DEVELOPMENT ASSISTANCE DEVICE

BACKGROUND

1. Technical Field

The disclosed device is in the fields of medical care education, emotional support for hospitalized children and their loved ones, and infant cognitive development and more specifically to a new and useful educational, support, and assistance device for use in the aforementioned fields.

2. Summary of the Art

Each year, nearly 500,000 babies are premature (i.e. babies that have completed less than 37 weeks of gestation). That's 1 of every 8 infants born in the United States. Important growth and development occur throughout pregnancy—especially in the final months and weeks. About 10 percent of all newborns in the United States need special medical care in a neonatal intensive care unit, or NICU due to birth defects, prematurity, or problems associated with delivery.

Advances in neonatal care, such as surfactant therapy and antenatal corticosteroids, are now widely available and have increased the survival of infants admitted to the NICU. However, studies of these vulnerable infants have demonstrated moderate-to-severe deficits in academic achievement, intellectual disabilities, and behavior problems, which correlate strongly with extended stays in NICUs. One potential cause is that these infants receive minimal human interaction during a time when typical healthy infants are being provided with nearly constant contact with their parent(s). Thus, there is a great need for a device that provides infants in NICUs with emotional and intellectual stimulation.

With respect to child development, it is understood that the nervous system of each human being must go through a definite series of developmental stages before a brain can operate at its full potential. Substantial negative consequences may result from a child delaying or missing a phase in this developmental sequence because of lack of opportunity. Being confined to an isolette, NICU patients often don't get the opportunity for frequent close-contact with caregivers that can provide opportunities to focus on high-contrast images like the ins next to the sclera. Putting high-contrast images in a baby's environment provides a focal point for a baby's attention, which allows him to lengthen his attention span, which in turn improves cognitive abilities. A device that provides opportunities to focus on high-contrast images in an environment that provides emotional support through familiar sounds would be a significant tool to help patients confined to isolettes.

While there are many recordable books, there are no books that provide for the unique needs of parents with children in long-term or intensive care. A book that can play a recording of a mother's voice or other loved one while in isolation can be a significant emotional support. Other calming sounds like the ocean or a heartbeat may also reduce the stress felt by the patient. Furthermore, if this book could be sterilized and placed in a more critically regulated environment like an isolette, it could also provide significant developmental assistance in one device which is not currently available.

Providing an auditory and visual medium wherein parents or guardians of hospitalized newborns and children can have their concerns eased through being familiarized with the procedures, equipment, and facilities being utilized to medically care for their infant or children would be of great benefit; however, there are no currently available devices which have addressed this problem.

SUMMARY OF THE INVENTION

A multi-page illustrated and written book printed on synthetic paper with an electronics module that can record sounds through one or more microphones to solid-state, digital memory and playback pre-recorded or user recorded audio data from the digital memory device through one or more speakers is disclosed. The book can include one or more of the following either on the front or back cover or on any of the plurality of pages inside the book: mirror, signature page, pocket page, or high-contract geometric patterns.

The book can be sterilizable using sterilizing hand wipes.

The electronics module can be powered with battery power or through wired power. Battery power for the device can be achieved through one or more replaceable batteries or through one or more fixed, rechargeable batteries.

The recording and playback functions provided by the electronics module can be activated and stopped manually or automatically through combinations of button presses, switches, and/or page turns. The buttons and/or switches can be mounted on any of the pages or covers of the book.

The output volume of the speakers can be adjusted manually or automatically by the electronics module. The automatic volume adjustment can use one or more of the speakers and/or microphones to sample background noise directly or to calculate the degradation of a known sound sample played through one or more of the speakers and re-recorded with one or more of the microphones.

The electronics module can play any combination of user recorded sounds (especially a mother's voice), pre-recorded instructions, or pre-recorded music or other sounds like the ocean, a heartbeat, or machine noises.

The electronics module can provide feedback to the user with lights, sounds, or other display means.

The electronics module can be connected to an external source to enable downloading and/or uploading of audio files onto the solid-state, digital memory.

The device can support non-human animals for ambulation and perform as explained elsewhere herein for humans.

LIST OF REFERENCE CHARACTERS

100: Device Assembly
105: Front Cover
110: Electronics Housing
115: Electronics Housing Cover Plate
120: Book Page
125: Book Spine
130: Speaker Sound Ports
135: Microphone Sound Ports
140: Recording Indicator Light
145: Device Status Indicator
150: Battery Charge Indicator
155: Data and Charging Port
160: Mirror
165: Geometric Patterns
170: Battery
175: Printed Circuit Board
180: Microphone
185: Speaker
190: Electronics Enclosure Slot
200: Page Selection Switch—Left
205: Page Selection Switch—Right
210: Parent 1 Switch
215: Parent 2 Switch
220: Human Heartbeat Switch
225: Ocean Sounds Switch
230: Custom Sounds Switch
235: Play All Switch
240: Automatic Playback Switch
245: Recording Lockout Toggle Switch
250: Membrane Switch Contact—Left
255: Membrane Switch Contact Right
260: Flexible Circuit

DETAILED DESCRIPTION

Figure 1:
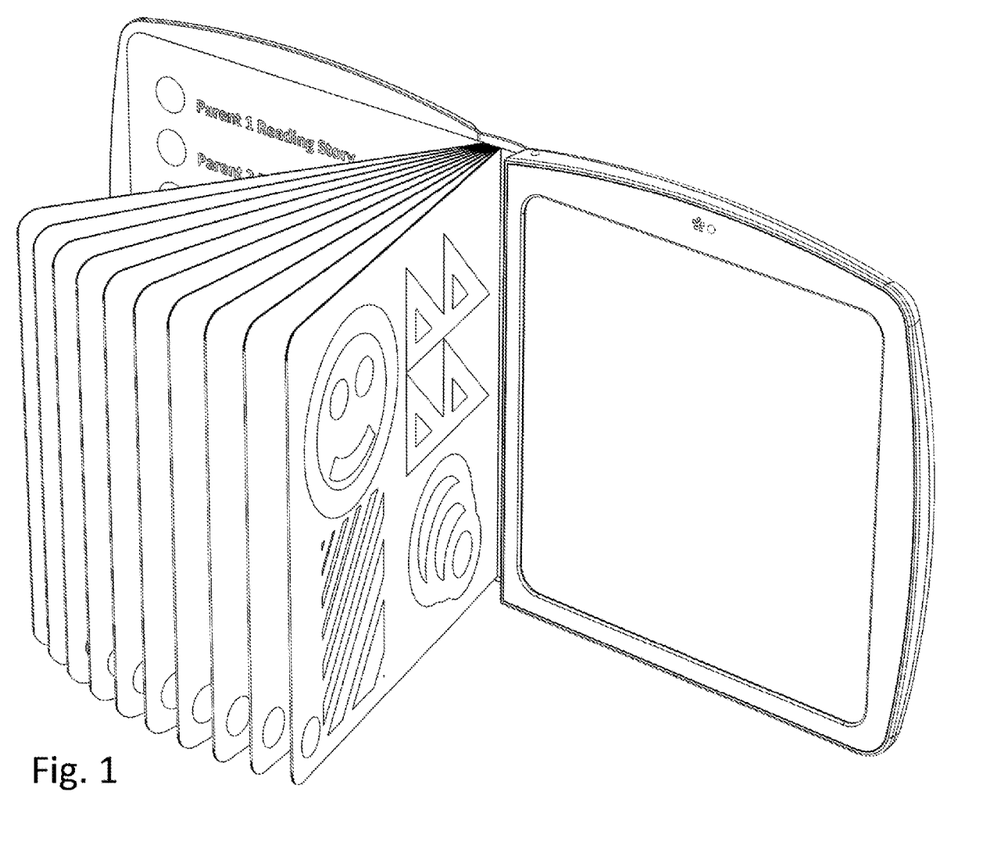
FIG. 1 is a perspective view of the inside of the device in an opened state.

FIG. 1 shows the device in an opened state. The foundational element of the device is a book, publication, or other similar source of visual information. The information contained therein can relate to medical procedures, equipment, specialized staff, and hospital environment. It can also contain information relating to diseases, physical abnormalities, health, and other short-term or chronic medical conditions. The information can be presented as a story wherein the main character in the story has a medical situation or condition.

Figures 2, 3:
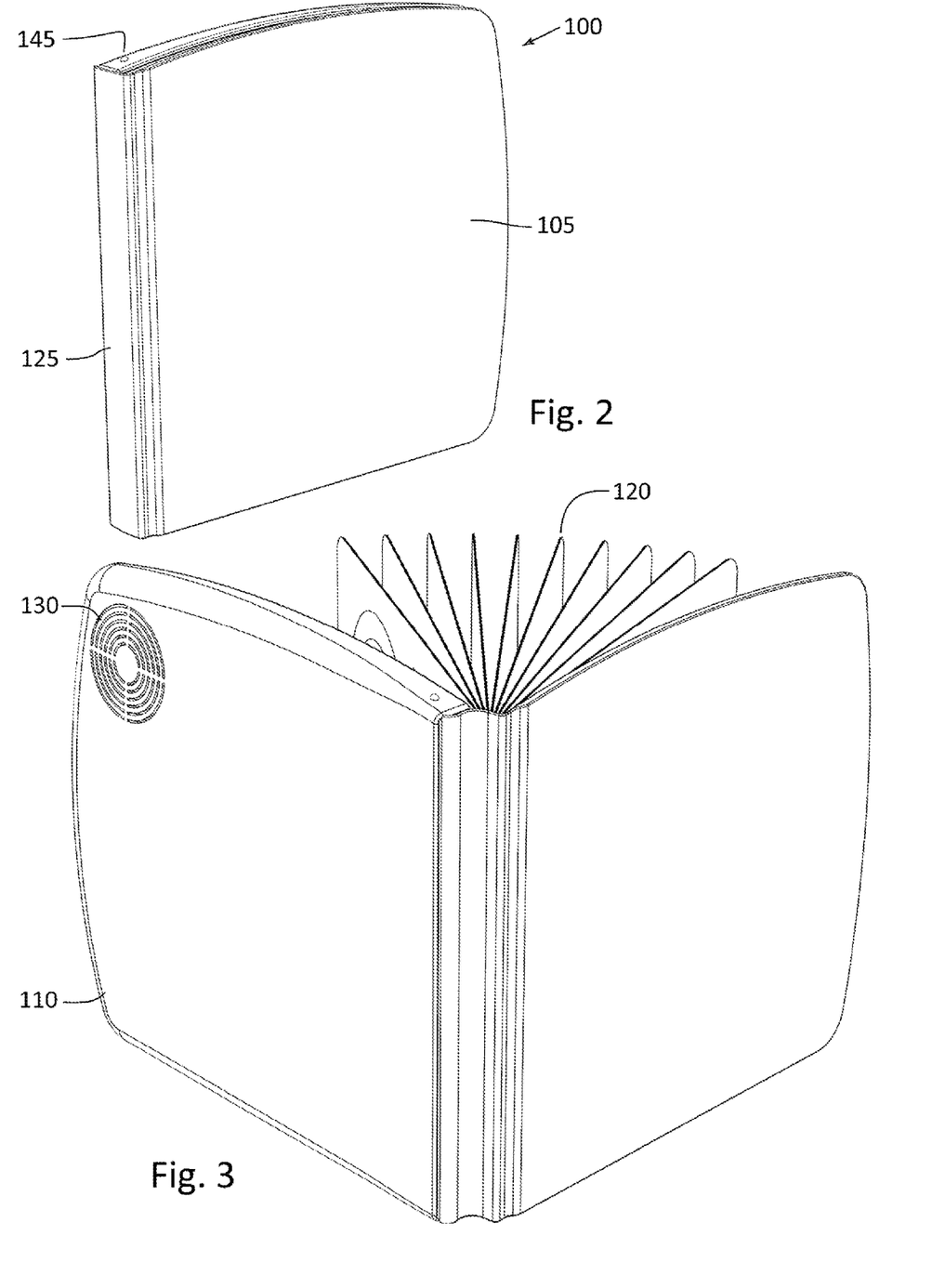
FIG. 2 is a perspective view of the device in a closed state.
FIG. 3 is a perspective view of the outside of the device in a partially opened state.
Figure 7:
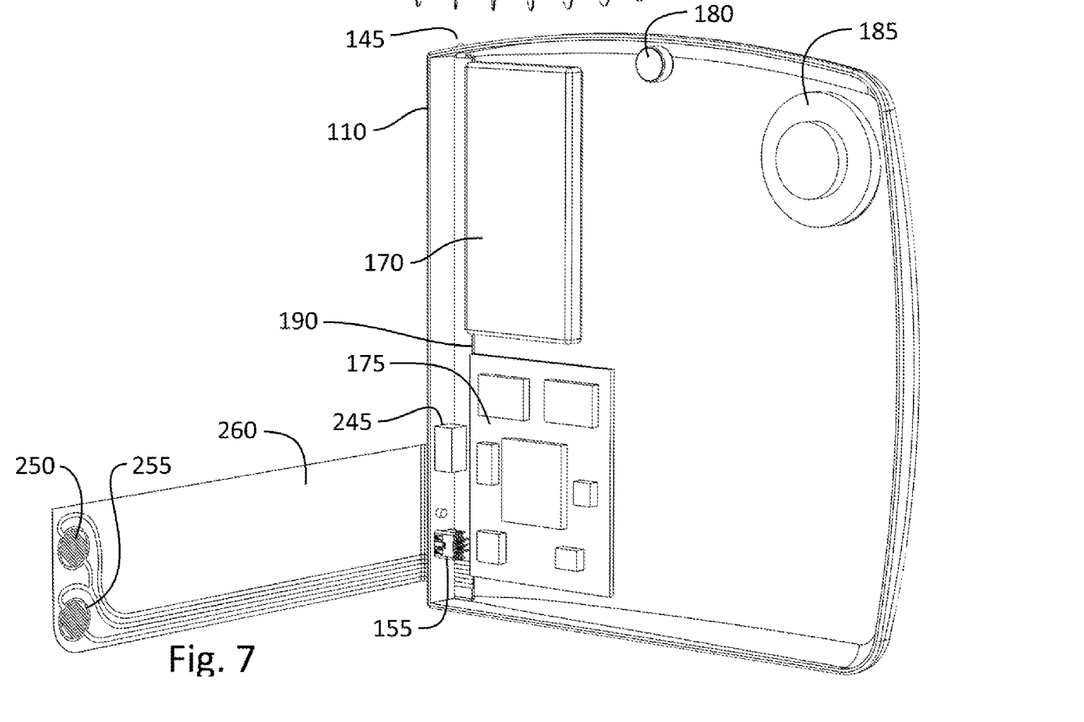
FIG. 7 is a perspective view of the inside of the device electronics housing and a flexible in-page circuit and switch.

FIG. 2 shows the device 100 in a closed state and FIG. 3 shows the device in a partially opened state. The front cover 105 is used to provide protection for the pages 120 of the book and depending on the composition, to provide structural rigidity. The spine 125 allows adequate flexibility for the device to be easily opened, yet is resilient enough to maintain retention between the front cover 105, electronics housing 110, and pages 120. The cover and spine can be manufactured with methods as are utilized for common books and publications. The pages 120 can be assembled from many separate pages, multiple folded pairs, or one long length of material that is folded like an accordion and then bonded together. The pages can be die-cut before or after folding. The materials used for the cover 105, spine 125, and pages 120 can be resistant to water and chemicals used for recurring sterilization in medical applications, such as synthetic paper. Alternatively, coatings and films can be applied to chemical/water non-resistant materials to achieve adequate performance in a hospital/medical environment. Adhesives, binding, and mechanical fastening materials utilized can be of sufficient water/chemical resistance and strength to assure the device will maintain sufficient bonding throughout the life of the device. The electronics housing 110 can act as the back cover of the device as well as a liquid resistant enclosure for much of the electronics components (FIG. 7). The housing can be manufactured from a wide range of plastic materials, including polymers that are resistant to medical sterilization chemicals, using one or more known plastics manufacturing techniques, such as injection molding. The water/chemical resistant design of the device can allow for relatively easy cleaning and sterilization if it, is contaminated (e.g. urine, feces, blood, etc.) The electronics housing 110 can also be configured similarly to the wide array of other commercially available audio book variants. For instance, some audio books have their enclosure located along one of the edges (top, side, bottom) of the book. The speaker sound ports 130 transmit sound from the speaker 185 (FIG. 7) to the outside of the electronics housing 110. The speaker sound ports 130 may also be located on other aspects of the electronics housing 110 to achieve adequate sound amplitude and quality.

Figure 4:
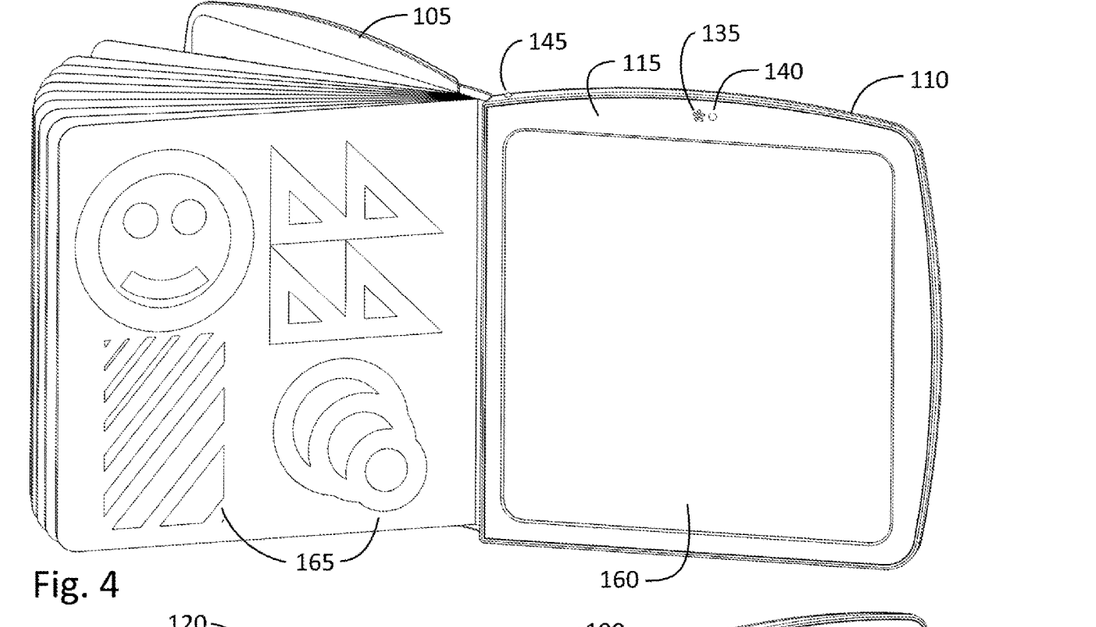
FIG. 4 is a perspective view of the inside of the device in an opened state, focused on the inside of the rear cover (electronics housing)
Figure 5:
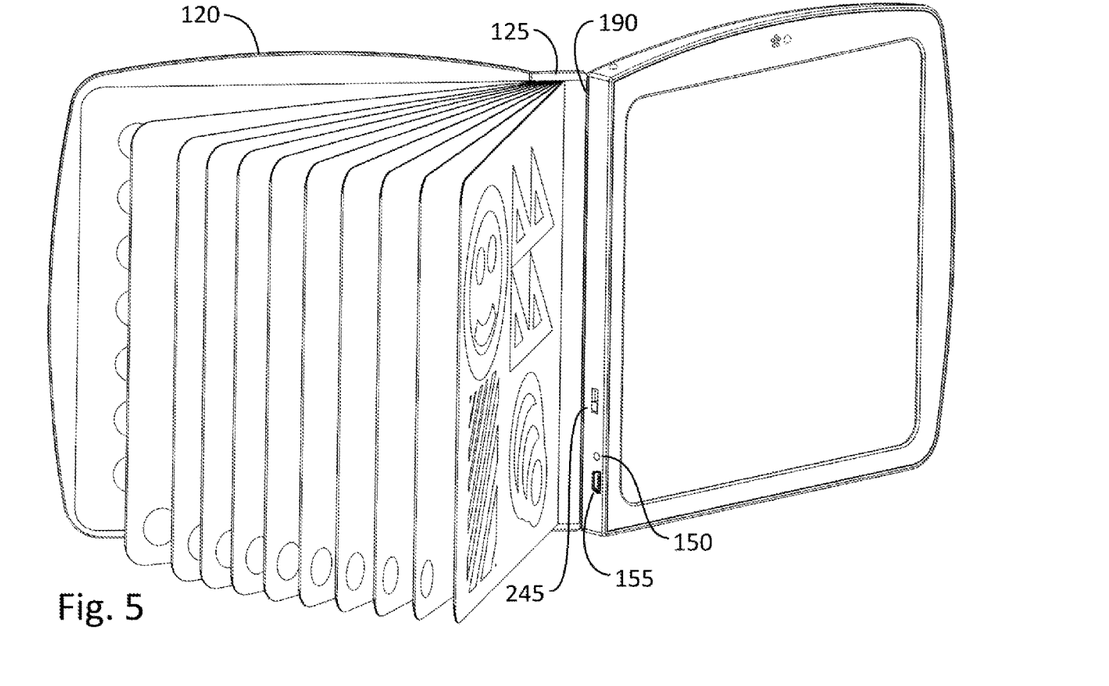
FIG. 5 is a perspective view of the inside of the device in an opened state, focused on the inside edge of the electronics housing.
Figure 8:
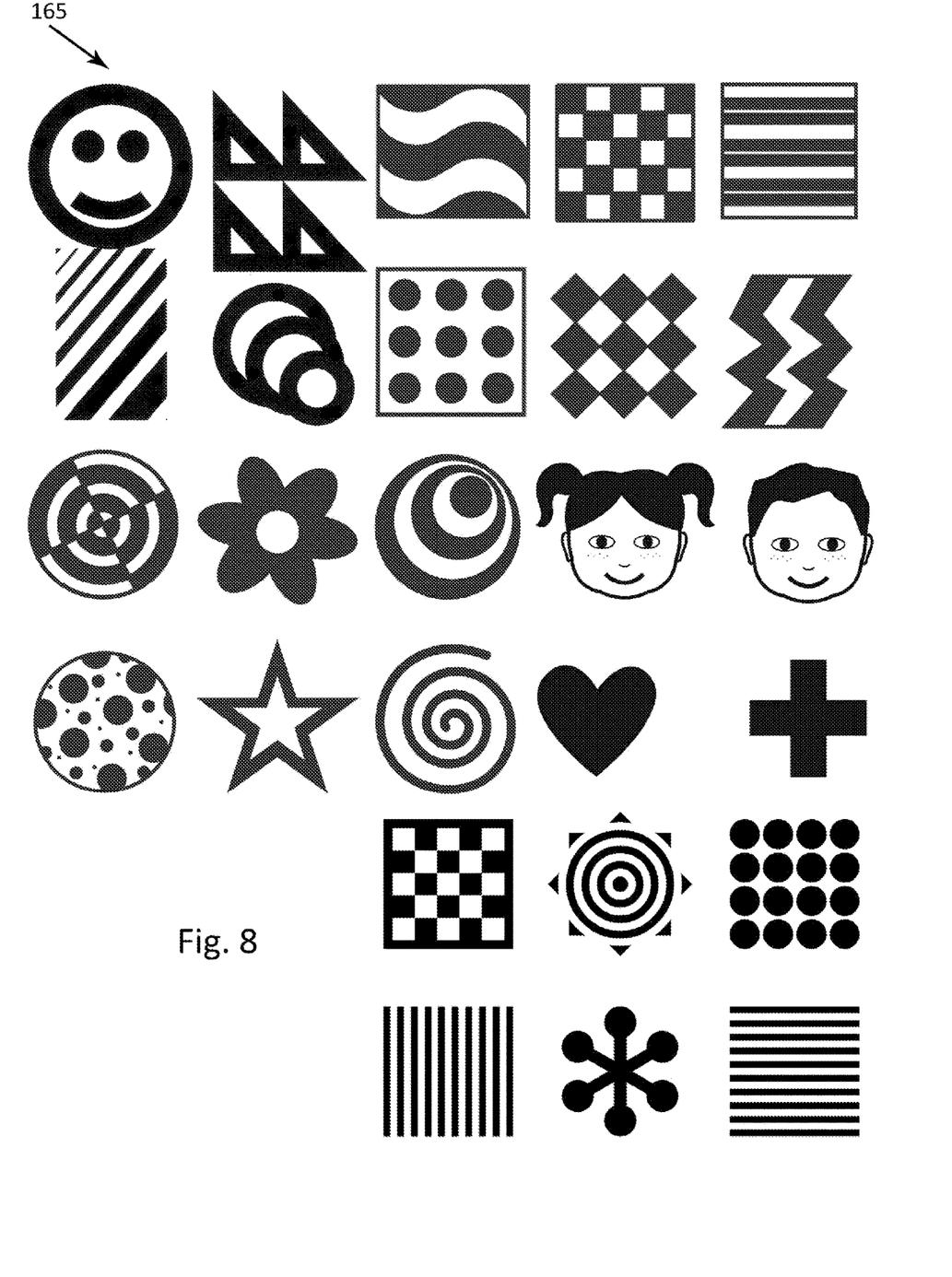
FIG. 8 illustrates examples of geometric patterns.

FIGS. 4 and 5 show the device in an opened state. The electronics housing cover plate 115 is attached to the open face of the electronics housing 110. The cover plate 115 can also be utilized to locate a mirror 160, microphone sound ports 135, and recording indicator light 140. The mirror 160, shown located on the electronics housing cover plate 115, can also be located within the electronics housing 110 such that it can be slid out through a slot (not shown) when needed. The mirror can also be located such that it replaces or covers the front cover 105, or outer aspect of the electronics housing 110 when the device is in a closed state. The mirror can be permanently positioned in the aforementioned locations, or it can be located via fixed or articulating attachment hardware (not shown). The mirror can be manufactured from a material that is shatter resistant (e.g. polycarbonate or acrylic) and can be scratch resistant. The geometric patterns 165 with non-limiting examples illustrated in FIGS. 4 and 8, can be an infinite variety of high-contrast shapes. These geometric patterns can be printed on any of the pages 120, the front cover 105, the outside aspect of the electronics housing, on a movable surface (not shown) that can be extended out from within the electronics housing 110 as needed. The geometric patterns can also be printed on a surface that is supported via articulating hardware (not shown). The microphone sound ports allow for sound to penetrate the electronics housing cover plate to reach the microphone 180 (FIG. 7). The recording indicator light 140 provides a visual indication that recording has begun or stopped. Device status indicator 145 can provide various status information to the caregiver or other users. The indicator 145 can be located such that it is easily visible when being viewed from the outside of an isolette or other infection control isolation system. For example, the indicator can show when playback is occurring, it can prompt the care-giver to begin playback again, it can warn of a low-battery condition, or it can indicate what mode the device is in. Data and charging port 155 can be configured as one of many commonly available interconnect standards (e.g. USB, mini-USB, micro-USB, Firewire, etc). This port 155 can be utilized to power the device, charge the internal batteries 170 (FIG. 7), or transmit/receive data. Battery charge indicator 150 can indicate the remaining battery power and/or charging status. The several aforementioned indicators can be single or multi-color light emitting diodes (LEDs), electroluminescent, or other light emitting devices. Electronics enclosure slot 190 can accept the book spine 125, book page(s) 120, and/or flexible circuits 160. Recording lockout toggle switch 245 can act to write-protect audio recordings when in the locked position, or allow recording in the unlocked position.

Figure 6:
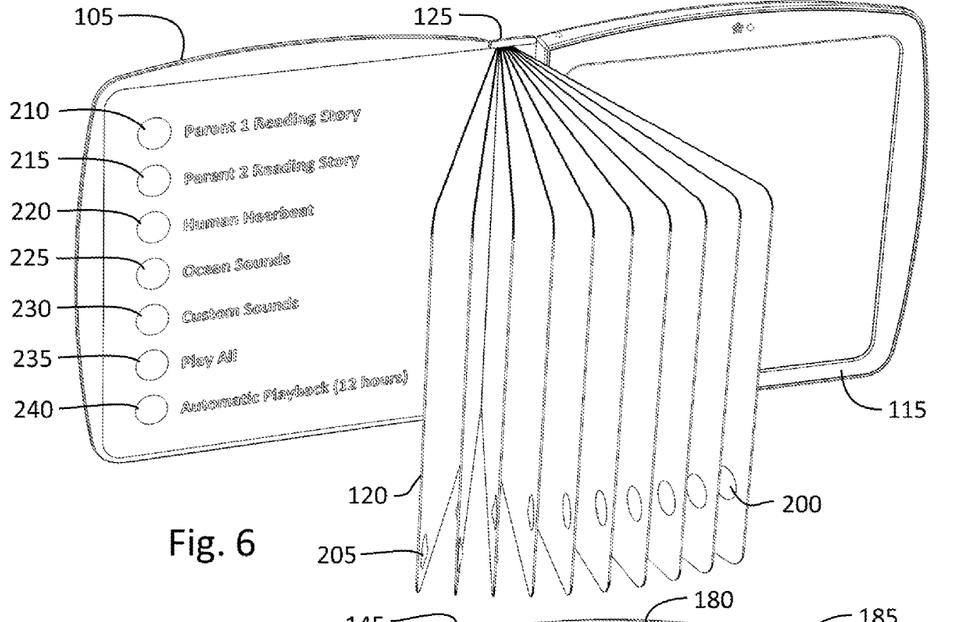
FIG. 6 is a perspective view of the inside of the device in an opened state, detailing the inside of the front cover and pages.

FIGS. 6 and 7 show an example button layout for the device, Inside the front cover 105, buttons can exist for playing back pre-recorded (220, 225) or user-recorded audio (210, 215, 220, 230), and initiating/cancelling automated playback (235, 240). Each page 120 can have one or more buttons that control recording, playback, and or other functions for that page. The left page selection switch 200 can be located on the left face of a page 120 and the right page selection switch 205 can be located on the right. The buttons 200 and 205 can be staggered such that activating the button on the opposite side of a page is less likely. The aforementioned buttons located on pages 120 and cover 105 can be of membrane switch type (e.g. 250 and 255) and be located on one or more flexible circuits (e.g. 260). However, other types of switches and circuits may also be adequate. The flexible circuits 260 can be separate units for each page or location (as shown in FIG. 7), or a longer continuous accordion circuit that serves more than one page 120. The flexible circuit 260 (FIG. 7) illustrates a potential circuit for a page 120 with one button on each side of the page. The left membrane switch contact 250 can be located below a dome feature (e.g. 200) embossed in the page. Similarly, the right membrane switch contact 255 can be located below a dome feature 205) embossed in the page. A common metallic foil or stamped/formed thin sheet metal component (not shown) can be used to complete the circuit of the membrane switch. Where the flex circuit is of continuous accordion design, the circuit folded over itself can be, used to make continuity. With the flexible circuit 260 located in the page 120 that has been folded over it, a void would exist in the locations of the page where no flexible circuit existed. This void can be filled with sheet material (not shown) of similar thickness to the flexible circuit in, order to maintain page thickness uniformity. The processor (not shown) on the PCB 175 can detect what button being pressed by having separate circuits for each switch, or by ensuring that each switch circuit has an adequately different resistance, such that the resistance value can be used to differentiate between all of the switches. Battery 160 can be used to store power such that the electronics can operate without being continuously connected to an outside power source. The battery can be of any type, including primary non-rechargeable batteries if the device is designed to accept them. Speaker 185 can emit audible sounds stored within the memory (not shown) located on printed circuit board 175. The electronics located on the PCB 175 can be configured to maintain, a playback level that is below the amplitude that could damage the hearing of anyone listening in close proximity (typically no higher than 80 decibels) to the speaker 185. Microphone 180 can allow the user to record their voice and for the device to monitor the environment for noise. The printed circuit board (PCB) 175 can be configured to record, store, and playback audio. The PCB can manage the usage of power from the data and charging port 155 and the battery 170. The PCB can control the indicator lights (e.g. 140, 145, 150) and microphone 180, as well as monitoring the status of the switches (e.g. 200, 205, 210, 215, 220, 225, 230, 235, 240, 245). The PCB can process audio signals to adjust payback levels, remove or reduce background noise, and make operational other decisions. Other page selection methods employed with commercially available recordable books are functional with this device. For example, photo-sensors, magnets, non-page-located switches may be utilized in conjunction with or replacement for the membrane switches (e.g. 250) described herein. A signature page (not shown) can provide a place for people to write good wishes. Pockets (not shown) on selected, pages or other locations within the device (not shown) can be utilized to store keepsakes (not shown).

One of many methods for using this device includes the following: A parent/guardian has an infant who is isolated in a neonatal intensive care unit (NICU). In this situation the parent may feel like they're abandoning or neglecting their newborn, they can feel scared due to not understanding the complex nature of the medical care their newborn is receiving, and the infant can be at risk for short-term as well as long-term developmental disadvantages due to their isolated environment and lack of stimulus. The healthcare provider or another source can provide the device 100 to the parent/guardian. The device contains a story (printed and audible) that describes various aspects of the medical condition and environment their newborn is in. The parents read (printed on pages 120) or listen to instructions (emitted from speaker 185), by pressing a button (not shown), with said instructions stored on PCB 175. The instructions direct them to read aloud the story within the pages 120 of the device. To begin they switch the recording lockout toggle switch 245 to the unlocked position. Starting on the first page 120 of the story, the parent pushes the button (e.g. 200, 205) on that page to initiate recording via microphone 180. When the device is ready to record it may play a noise and/or illuminate the recording indicator light 140 to inform the user that they can read the story aloud. When the user has completed recording, they can press the same button they used to initiate recording. The user may be able to playback a pre-recorded version of the story prior to recording their own by using a certain sequence or duration of button presses. Likewise, the user may playback, delete, or re-record using various durations or sequences. Following recording the story on each page, the user may choose to have the other parent or a relative record their voice reading the story. The user may be given the option of recording other custom messages as well. Once all of the audio recordings have been made, the user can move the recording lockout toggle switch to the locked position to preserve the recordings.

The user can then provide the device back to the healthcare provider or to the staff in their infant's care center. The staff in the care center can sterilize the device with chemicals and procedures standardized for their facility to minimize the chance that infectious contaminants will reach the isolated infant. The medical staff can leave the device in the isolette with the infant and activate the audio playback manually or semi-automatically, or automatically via the buttons on the front cover (e.g. 210, 215, 220, 225, 230, 235, 240, 245). Semi-automatic playback can include randomly playing through each of the audio files stored randomly for a particular period of time or until a button is pressed. Automatic playback can include monitoring the environment with the microphone 180 for crying or other noises and then playing audio back in response. The infant can be soothed and comforted by listening to the sound of their parent's voice and the pre-recorded sounds. The medical staff can make the geometric patterns 165 and/or the mirror 160 visible to the infant. The geometric patterns can provide the infant with improved development by viewing them, thereby improving their medical outcome. The mirror 160 can allow the infant the ability to see him or herself, which can improve their medical outcome as well. Following the infant's release from the medical facility, the parents/guardians can take the device home as a keepsake. A signature page can be signed by relatives and friends of the family. If the device is contaminated during use (e.g. urine, feces, blood, etc.), then it can be easily cleaned per standard medical facility protocols.

Another scenario includes children with medical conditions who can read and/or understand the written word, and/or who may also be separated from one or both parents/guardians. In this situation the device can be used to help the older child understand the various aspects of their situation similarly to how the parents/guardians were able to understand their infant's situation in the situation presented above. Additionally, the child can read and record the story themselves in an effort to better understand their situation.

It is therefore intended that the forgoing detailed description be regarded as illustrative rather than limiting, and that it be understood that it is the following claims, including all equivalents that are intended to define the spirit and scope of this disclosed device. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A book, comprising:
   a rigid front cover comprising a front cover inner side and a front cover exterior, wherein the front cover inner side comprises a plurality of front cover audio playback buttons;
   a back cover connected to the front cover by a spine, wherein the back cover comprises a back cover exterior and a back cover inner side, wherein the back cover comprises a liquid-resistant enclosure housing a plurality of electronic components, wherein the plurality of electronic components comprises:
      a printed circuit board (PCB) comprising a processor and a memory unit,
      a microphone controlled by the processor on the PCB,
      one or more speakers controlled by the processor on the PCB, and
      a battery configured to power the electronic components,
         wherein the microphone is configured to record audio generated by a user and digitally store such an audio recording in the memory unit,
         wherein pressing the at least one of the plurality of front cover audio playback buttons causes the audio recording or a pre-recorded audio recording stored in the memory unit to be played via the one or more speakers;
   a plurality of pages connected to the spine and positioned in between the front cover and the back cover,
      wherein the plurality of pages are made of at least one of a synthetic paper, a non-synthetic paper with a coating applied thereto, and a non-synthetic paper with a film applied thereto, wherein the plurality of pages are configured to withstand sterilization in a healthcare setting,
      wherein at least one of the plurality of pages comprises a high-contrast geometric pattern printed or otherwise applied onto the page,
      wherein at least one of the plurality of pages comprises a first button on a first side of a page and a second button on a second side of the same page, wherein the page comprises a void space within the page, wherein the first button and the second button are connected to the PCB via one or more flexible circuits positioned within the void space, wherein the plurality front cover audio playback buttons are connected to the PCB via the one or more flexible circuits or additional flexible circuits, wherein a positioning of the first button on the page is staggered with respect to the positioning of the second button on the page, and wherein pressing at least one of the first button and the second button causes the audio recording or the pre-recorded audio recording stored in the memory unit to be played via the one or more speakers; and
   a shatter-resistant mirror coupled to the rigid front cover or the back cover.

2. The book of claim 1, wherein the shatter-resistant mirror is detachably coupled to the back cover, wherein the shatter-resistant mirror is configured to be slid into or out of the enclosure via a slot defined along the enclosure.

3. The book of claim 1, wherein the shatter-resistant mirror is coupled to the rigid front cover.

4. The book of claim 1, wherein the shatter-resistant mirror is fixedly attached to the back cover inner side and configured to serve as a final page of the book.

5. The book of claim 4, wherein one of the plurality of pages is a page immediately preceding the shatter-resistant mirror serving as the final page of the book, and wherein the page immediately preceding the shatter-resistant mirror serving as the final page of the book comprises a plurality of high-contrast geometric patterns printed or otherwise applied on to the page.

6. The book of claim 4, further comprising a microphone sound port defined along an upper edge of the back cover inner side above the shatter-resistant mirror, wherein the microphone sound port is configured to allow sound to reach the microphone within the enclosure housing the microphone.

7. The book of claim 6, further comprising a recording indicator light positioned above the mirror along the upper edge of the back cover inner side, wherein the recording indicator light is configured to provide a visual indication that audio recording by the microphone is occurring or stopped.

8. The book of claim 7, further comprising a device status indicator light positioned along a top edge of the back cover such that the device status indicator light is visible to a user when the book is closed or opened, wherein the device status indicator is configured to provide a visual indication of a battery power level, an operating mode, or an audio playback status of the book.

9. The book of claim 1, wherein the plurality of front cover audio playback buttons, the first button, and the second button are membrane switch contacts.

10. The book of claim 9, wherein each of the plurality of front cover audio playback buttons, the first button, and the second button is implemented as a dome embossed on the page covering the membrane switch contact.

11. The book of claim 10, wherein the plurality of front cover audio playback buttons, the first button, and the second button are connected to the PCB via a plurality of flexible circuits.

12. The book of claim 10, wherein the plurality of front cover audio playback buttons, the first button, and the second button are connected to the PCB via one continuous flexible circuit configured to fold over itself in an accordion manner.

13. The book of claim 1, wherein the microphone is configured to monitor an environmental noise level or a patient-emitted sound and wherein the processor on the PCB is configured to automatically play the audio recording or the pre-recorded audio recording stored in the memory unit in response to the environmental noise level or the patient-emitted sound detected.

14. The book of claim 1, wherein the microphone is configured to monitor an environmental noise level and wherein the processor on the PCB is configured to automatically adjust a volume of the one or more speakers based on the environmental noise level detected.

15. The book of claim 1, wherein the back cover further comprises a recording lockout toggle switch positioned along an edge of the enclosure, wherein the recording lockout toggle switch comprises a locked position and an unlocked position, and wherein a previously recorded audio recording is protected when the recording lockout toggle switch is in the locked position.

16. The book of claim 1, wherein the memory unit is configured to be connected to an external source to enable downloading of the audio recording onto the external source or uploading additional pre-recorded audio recordings to the memory unit.

17. The book of claim 1, wherein the processor is configured to control the speaker to play the audio recording or the pre-recorded audio recording in a random order for a predetermined period of time or until at least one of the front cover audio playback buttons, the first button, and the second button is pressed.

18. The book of claim 1, wherein the processor on the PCB is configured to control a playback volume of the audio recording or the pre-recorded audio recording stored in the memory unit such that the playback volume is limited to 80 decibels.

19. The book of claim 1, wherein at least one of the plurality of pages comprises a pocket configured to store keepsakes.

20. The book of claim 1, wherein at least one of the plurality of pages comprises a page portion configured to receive a written signature.

* * * * *